United States Patent
Bourque et al.

(10) Patent No.: US 10,028,843 B2
(45) Date of Patent: Jul. 24, 2018

(54) COMPACTION PLIERS HAVING REMOVABLE CUTTING INSERTS

(71) Applicant: Smith & Nephew, Inc., Memphis, TN (US)

(72) Inventors: Bernard J. Bourque, Rehoboth, MA (US); William R. Davis, Hingham, MA (US); Alfred R. Berube, Jr., N. Attleboro, MA (US)

(73) Assignee: Smith & Nephew, Inc., Memphis, TN (US)

( * ) Notice: Subject to any disclaimer, the term of this patent is extended or adjusted under 35 U.S.C. 154(b) by 425 days.

(21) Appl. No.: 14/398,516

(22) PCT Filed: May 6, 2013

(86) PCT No.: PCT/US2013/039649
§ 371 (c)(1),
(2) Date: Nov. 3, 2014

(87) PCT Pub. No.: WO2013/169627
PCT Pub. Date: Nov. 14, 2013

(65) Prior Publication Data
US 2015/0112354 A1    Apr. 23, 2015

Related U.S. Application Data

(60) Provisional application No. 61/643,467, filed on May 7, 2012.

(51) Int. Cl.
*A61F 2/46*    (2006.01)

(52) U.S. Cl.
CPC .......... *A61F 2/4601* (2013.01); *A61F 2/4644* (2013.01); *A61F 2002/4602* (2013.01); *A61F 2002/4622* (2013.01)

(58) Field of Classification Search
CPC .................. A61F 2/4601; A61F 2/4644; A61F 2002/4602; A61F 2002/4622;
(Continued)

(56) References Cited

U.S. PATENT DOCUMENTS 5,329,846 A * 7/1994 Bonutti .............. A61B 17/1606
                                                            100/110
5,466,243 A   11/1995 Schmieding et al.
(Continued)

FOREIGN PATENT DOCUMENTS

EP    1 216 666 A2    6/2002
JP    2002-306517 A   10/2002
(Continued)

OTHER PUBLICATIONS

Office Action from related European Application No. 13724963.7 1654 dated Nov. 11, 2016.
(Continued)

*Primary Examiner* — Matthew Lawson
*Assistant Examiner* — Amy Sipp
(74) *Attorney, Agent, or Firm* — Burns & Levinson, LLP; Joseph M. Maraia

(57) ABSTRACT

A bone graft compaction pliers with removable inserts defines a bone graft harvesting and deployment system applicable to a wide variety of bone graft sized for use with bone anchors such as those employed in ACL repair. Cannulated bone anchors for encouraging bone regrowth employ an anchor with a axial cannulated bore and a plurality of fenestrations surrounding the bore to facilitate bone regrowth. A variety of sizes of single use inserts corresponding to a bone graft shape, or diameter, engage a single compaction pliers for forming various sized bone grafts from a single tool. A transparent transfer tube and corresponding base receives the formed bone graft for length (Continued)

adjustment, and engages protrusions on the recipient bone anchor for aligning the transfer tube to the anchor for disposing the bone graft into the cannulated bore of the anchor.

9 Claims, 13 Drawing Sheets

(58) Field of Classification Search
CPC .............. A61F 2002/4649; A61B 17/66; A61B 17/8019; A61B 2017/681
USPC ............................. 144/269; 604/250; 72/712
See application file for complete search history.

(56) References Cited

U.S. PATENT DOCUMENTS

| | | | |
|---|---|---|---|
| 5,718,707 A | 2/1998 | Mikhail | |
| 6,315,780 B1 | 11/2001 | Lalonde | |
| 7,635,364 B2* | 12/2009 | Barrall | A61B 17/7059 606/70 |
| 8,579,950 B1* | 11/2013 | Jordan | A61B 17/8019 606/324 |
| 8,685,037 B1* | 4/2014 | Jordan | A61B 17/8019 606/105 |
| 2001/0008979 A1* | 7/2001 | Bonutti | A61B 17/1606 623/13.17 |
| 2002/0082604 A1 | 6/2002 | Abdelgany et al. | |
| 2004/0034437 A1* | 2/2004 | Schmieding | A61B 17/1615 623/20.14 |
| 2004/0127906 A1* | 7/2004 | Culbert | A61B 17/70 606/247 |
| 2006/0116683 A1* | 6/2006 | Barrall | A61B 17/7059 606/71 |
| 2006/0247642 A1 | 11/2006 | Stone et al. | |
| 2007/0093896 A1 | 4/2007 | Malinin | |
| 2008/0027471 A1 | 1/2008 | Hauri | |
| 2009/0222052 A1 | 9/2009 | Vandewalle et al. | |
| 2010/0012704 A1 | 1/2010 | Tarinelli Racenet et al. | |
| 2010/0072251 A1 | 3/2010 | Baxter, III et al. | |
| 2011/0184426 A1 | 7/2011 | Garces Martin et al. | |
| 2013/0000051 A1* | 1/2013 | Cleland | B23D 21/02 7/128 |

FOREIGN PATENT DOCUMENTS

| | | |
|---|---|---|
| JP | 2003-024341 A | 1/2003 |
| JP | 2005-013740 A | 1/2005 |
| JP | 2010-119860 A | 6/2010 |
| RU | 2212865 C1 | 9/2003 |
| RU | 2322209 C1 | 4/2008 |
| SU | 951881 A1 | 9/1982 |

OTHER PUBLICATIONS

Patent Examination Report from related Australian Application No. 2013259852 dated Nov. 16, 2016.
Office Action from related Japanese Application No. 2015-511564 dated Feb. 27, 2017.
International Search Report, PCT/US2013/039649, dated Sep. 4, 2013.
Second Office Action from related Chinese Application No. 201380024103.5 dated Jun. 1, 2016.
Office Action from related Russian Application No. 2014148097/14(077387) dated Apr. 6, 2017.

* cited by examiner

COMPACTION PLIERS HAVING REMOVABLE CUTTING INSERTS

BACKGROUND

Reconstructive surgical procedures often attach donor and prosthetic connection members to structural skeletal members of a patient. Often, bone grafts provide surgical attachment of reconstructive components such as tendons, ligaments, and prosthetic anchors. Various methods of attaching tissue, such as soft tissue, grafts or ligaments to bone have been employed. In anterior or posterior cruciate ligament reconstruction (ACL or PCL), for example, conventional approaches employ interference screws used to secure the graft against the walls of tunnels drilled in the tibia and the femur. The interference screws are wedged between the graft and a wall of the tunnel. To facilitate insertion and improve anchoring, some interference screws include cutting threads or other anchoring features. Alternately, in performing hip prosthesis surgery, it is frequently necessary or desirable to place bone graft material in the intramedullary canal of the femur in order to promote new bone growth. Insertion of harvested bone material at a surgical site facilitates regeneration of bone around the inserted anchors.

SUMMARY

A bone graft compaction pliers with removable inserts defines a bone graft harvesting and deployment system applicable to a wide variety of bone graft sizes for use with bone anchors such as those employed in ACL repair. Cannulated bone anchors for encouraging bone regrowth employ an anchor with an axial cannulated bore and a plurality of fenestrations surrounding the bore to facilitate bone regrowth into and around the inserted anchor for strengthening the bone anchor and mitigating possible complications with exposed foreign surfaces at a surgical site. A variety of sizes of single use inserts corresponding to a bone graft shape, or diameter, engage a single compaction pliers for forming various sized bone grafts from a single tool. A transparent transfer tube and corresponding base receives the formed bone graft for length adjustment, and engages protrusions on the recipient bone anchor for aligning the transfer tube to the anchor for disposing the bone graft into the cannulated bore of the anchor.

Configurations herein are based, in part, on the observation that conventional approaches to bone graft harvesting and insertion techniques encounter difficulties in matching the size of the graft to the size of the anchor cannula or bone hole to which the graft is to be inserted. Unfortunately, conventional approaches to bone graft deployment suffer from the shortcoming that substantial pressure and force are required to properly form the bone graft from harvested bone material, typically requiring sturdy metal tools, yet the surgical nature of the procedure mandates either single-use materials or extensive cleaning and sterilization. Considerable expense may be associated with the range of tools needed to anticipate a variety of bone graft sizes.

Accordingly, configurations herein substantially overcome the above-described shortcomings by providing a compression pliers with removable single-use inserts sized to particular bone graft shapes (typically cylindrical). A single compaction pliers is receptive to a range of inserts corresponding to the various sizes of bone grafts, thus allowing the unitary inserts to remain single use, mitigating production costs, and allowing a single tool to accommodate a variety of bone graft sizes. The tool remains reusable, thus imposing only resterilization of a single tool, rather than a range of tools otherwise required for different sized grafts. Alternatively, a single use compaction pliers would still only impose a single tool usable with multiple inserts, rather than multiple compaction pliers, each corresponding to a particular bone graft size.

Configurations herein disclose a bone graft formation and insertion device including a pair of pivotally coupled elongated handles having opposed compressive members drawn together in a compressive engagement by closure of the handles, such that each of the opposed compressive members, or jaws, has a receptacle for engaging an insert, the inserts in turn having compressive faces defining a compression cavity corresponding to a cannulated anchor, in which the cannulated anchor is receptive to a bone graft formed by drawing together and engaging the opposed compressive faces. Latches provide for detachable engagement with a plurality of inserts having different compressive faces.

The device performs a system and method for harvesting, forming and inserting bone grafts, by forming a bone graft between opposed compressive faces of a compaction pliers, such that each of the opposed compressive faces defines a removable insert corresponding to a shape of the bone graft, and transferring the bone graft to a transfer tube, such that the transfer tube has a shape corresponding to the shape of the bone graft for receiving the bone graft. A transfer block measures, during the transfer of the bone graft to the transfer tube, a length of the bone graft to correspond to a length of a receptive anchor for receiving the bone graft, following which the transfer tube is engaged to the receptive anchor, in which the anchor has been previously inserted in a surgical site and has a cannulated bore corresponding to the shape of the bone graft. A plunger inserts the bone graft into the cannulated bore by disposing the plunger through an opposed end of the transfer tube, in which the plunger corresponds to the shape of the transfer tube for driving the bone graft to a predetermined depth corresponding to the anchor.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
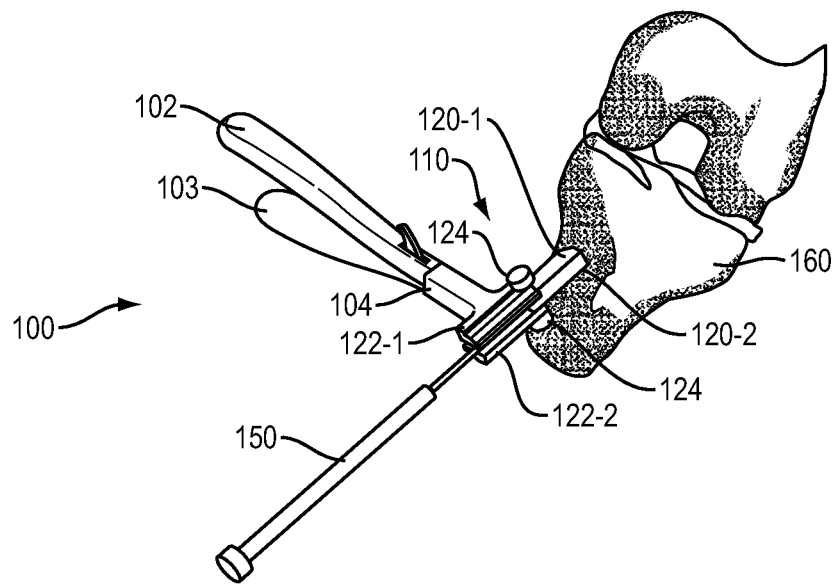
FIG. 1 is a context diagram of compaction pliers in a surgical environment.

FIG. 1 is a context diagram of compaction pliers in a surgical environment. Referring to FIG. 1, in ACL repair and other procedures, a compaction pliers 100 and corresponding removable inserts 120-1, 120-2 are employed as a surgical instrument for use with bone graft techniques. The compaction pliers 100 are a device for shaping harvest bone material to a consistent size corresponding to a bone tunnel (surgical excavation or hole) 110 for receiving the bone graft material. The compaction pliers 100 include cutting inserts 120-1, 120-2 (120 generally) on opposed jaws 122-1, 122-2 (122 generally) drawn together by closure of handles 102, 103 attached at a pivot point 104. The sliding and cutting insets 120 may be spring (FIG. 4) 128 loaded with knobs 124 to lock and slide around graft material while it is engaged and advanced into the surgical excavation 110, typically via a hand driven plunger tool. Alternatively, the inserts 120 may be latched onto the opposed jaws 122, both discussed further below.

Figure 2:
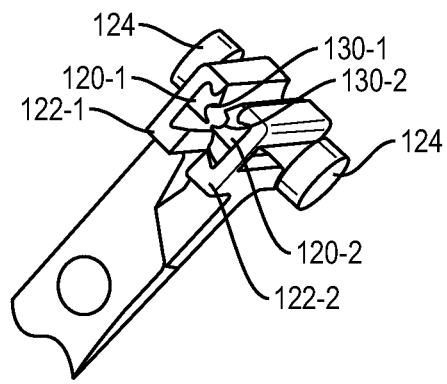
FIG. 2 is a perspective view of inserts in the compaction pliers of FIG. 1.

FIG. 2 is a perspective view of inserts in the compaction pliers of FIG. 1. In operation of the proposed approach, manual closure of handles 102, 103 forces a compression face 130-1 of the inserts 120 drawn to be into a compressive mating with a harvest material between an opposed compressive face 130-2 (130 generally). Each of the compression faces 130 is slideably engageable with the articulated jaws 122 that pivot to close the respective compressive faces 130 in engagement around the donor graft material such that the graft takes the shape defined by the faces 130. In a particular approach, the compression faces 130 define a cylindrical shape 132 flanked by axial cutting edges 134-1, 134-2 along each side of the cylindrical shape 132 and running parallel to the cylindrical axis.

Depicted below are various configurations of the surgical instrument including compaction pliers 100 having compressive faces 130 formed to define the desired shape 132 of a bone graft. The compaction pliers 100 perform a method of delivering compacted bone as bone graft material from the pliers 100 and into an attachment member, such as a screw or threaded member, for disposing the graft material into contact with native bone material for facilitating reconstructive growth. Bone graft material may be inserted directly into a bone tunnel, or may be inserted into a cannulated, fenestrated anchor for providing additional holding strength as the bone regrows around the anchor. Typically, the graft is a cylindrical size 132 substantially similar to a drilled receptacle (hole) 110 in the skeletal (bone) structure 160 for attachment. The compaction pliers 100 are therefore for use with bone graft techniques for shaping harvest bone material to a consistent size corresponding to a surgical excavation (graft hole) 110, in which the pliers include sliding and cutting inserts 120 attached by an retention mechanism, such as an engaging slot, or may be spring 128 loaded with knobs 124 to lock and slide around graft material on opposed jaws 122 drawn together by closure of handles 102, 103 attached at a pivot point 104.

Figure 3:
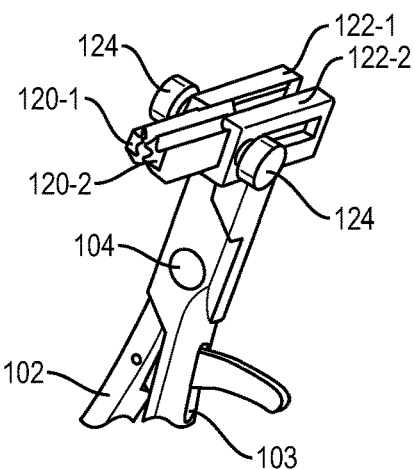
FIG. 3 is a perspective view of the sliding inserts of FIG. 2 partially disposed.
Figure 4:
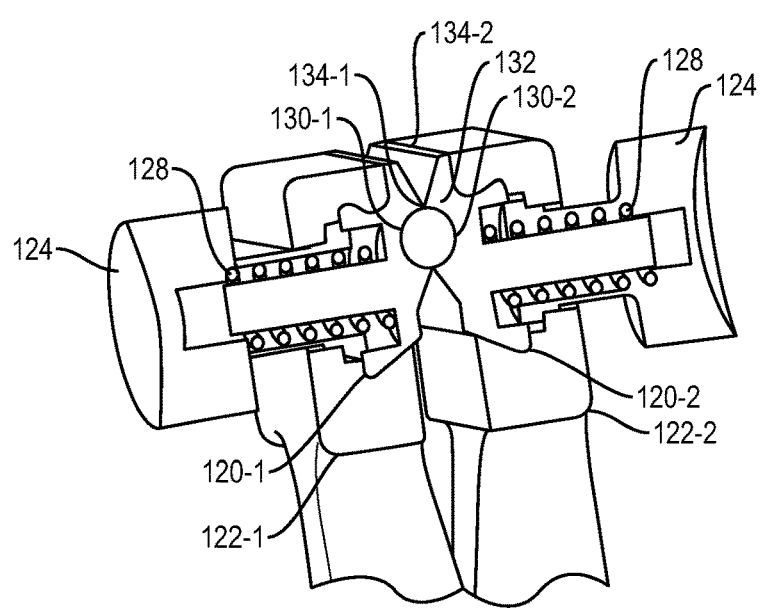
FIG. 4 is a cutaway view of a retention mechanism for retaining the sliding inserts of FIG. 3.

FIG. 3 is a perspective view of the sliding inserts of FIG. 2 partially disposed, and FIG. 4 is a cutaway view of a retention mechanism for retaining the sliding inserts of FIG. 3. Referring to FIGS. 3 and 4, in an example arrangement using a drill system for extracting donor bone, once the harvest bone is removed from a drill or other harvesting mechanism, the bone is shaped with the compaction pliers 100 to the predetermined size diameter 132. The sliding and cutting insets 120 have the ability to advance from one position to another position and lock in place. A plunger 150 (FIG. 11, below) is employed to push the shaped bone from the sliding and cutting inserts into the attachment member, such as a cavitized bone screw having a cannulated bore or void for receiving the graft material and maintaining contact with the native bone 160.

In operation, the knobs 124 are spring 128 loaded to lock and slide the inserts 120. The locking and sliding mechanism provides improved control and provides for a built in transfer insert.

Figure 5:
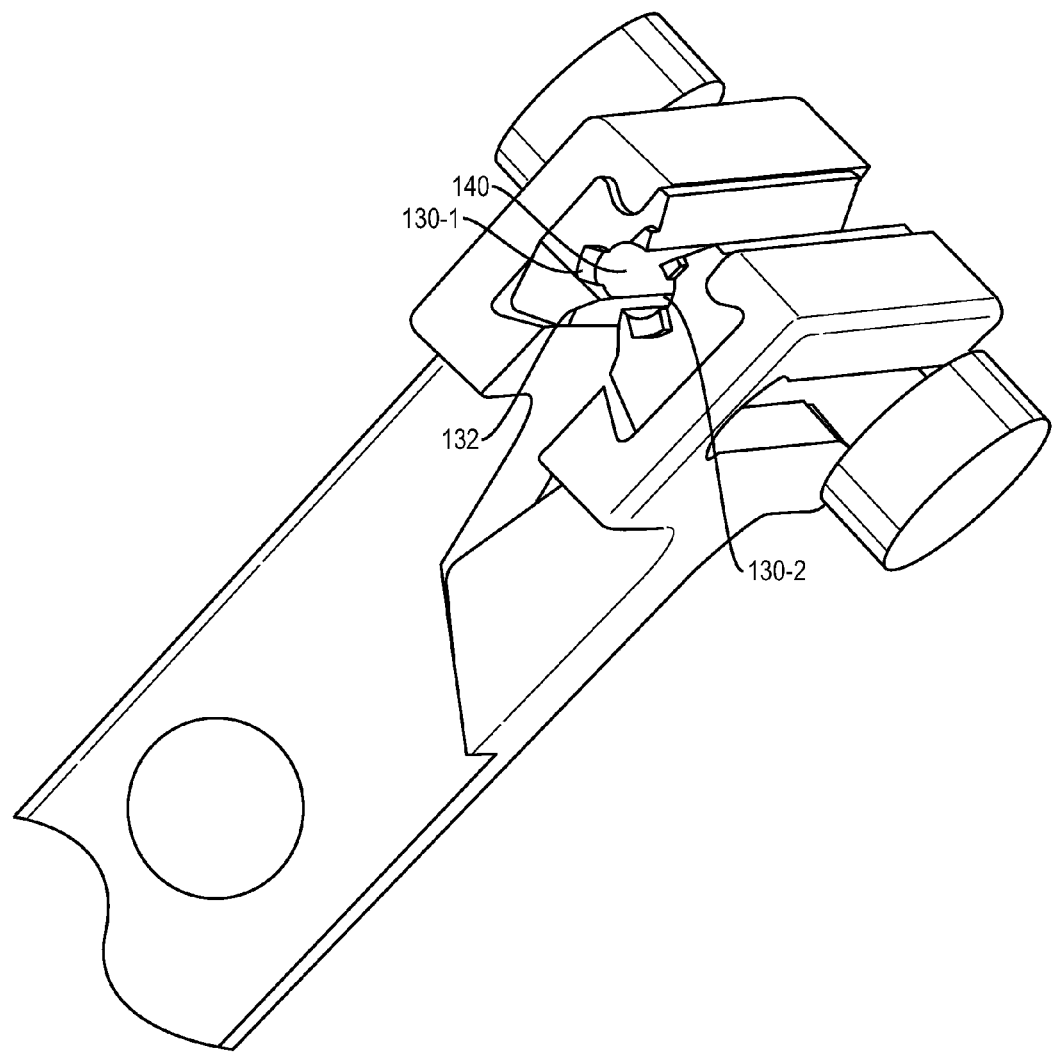
FIG. 5 is a perspective view of a compression cavity formed between a pair of opposed inserts.

FIG. 5 is a perspective view of a compression cavity 140 formed between a pair of opposed inserts. Referring to FIGS. 4 and 5, In contrast to conventional approaches, the proposed approach employs sliding and cutting inserts 120 anchored into articulated jaws 122 with spring loaded knobs 124 to slide and lock into place. The proposed approach further differs because a compression face 130-1 is drawn into a compressive mating with a harvest material between an opposed compressive face 130-2, and is slideably engageable with the articulated jaws 122 that pivot to close the respective compressive faces 130 to form the compression cavity 140. In the proposed approach, the compression faces 130 define a cylindrical shape 132 flanked by axial cutting edges 134-1, 134-2 along each side of the cylindrical shape 132 and running parallel to the cylindrical axis. The novel cutting edges 134 sever and extract excess harvest material resulting in a uniform cylindrical shape of the desired diameter. Conventional approaches do not employ opposed compression faces 130 pivotally coupled via articulated handles 102, 103 and drawn together in an arcuate manner via closure of the handles.

Figure 6:
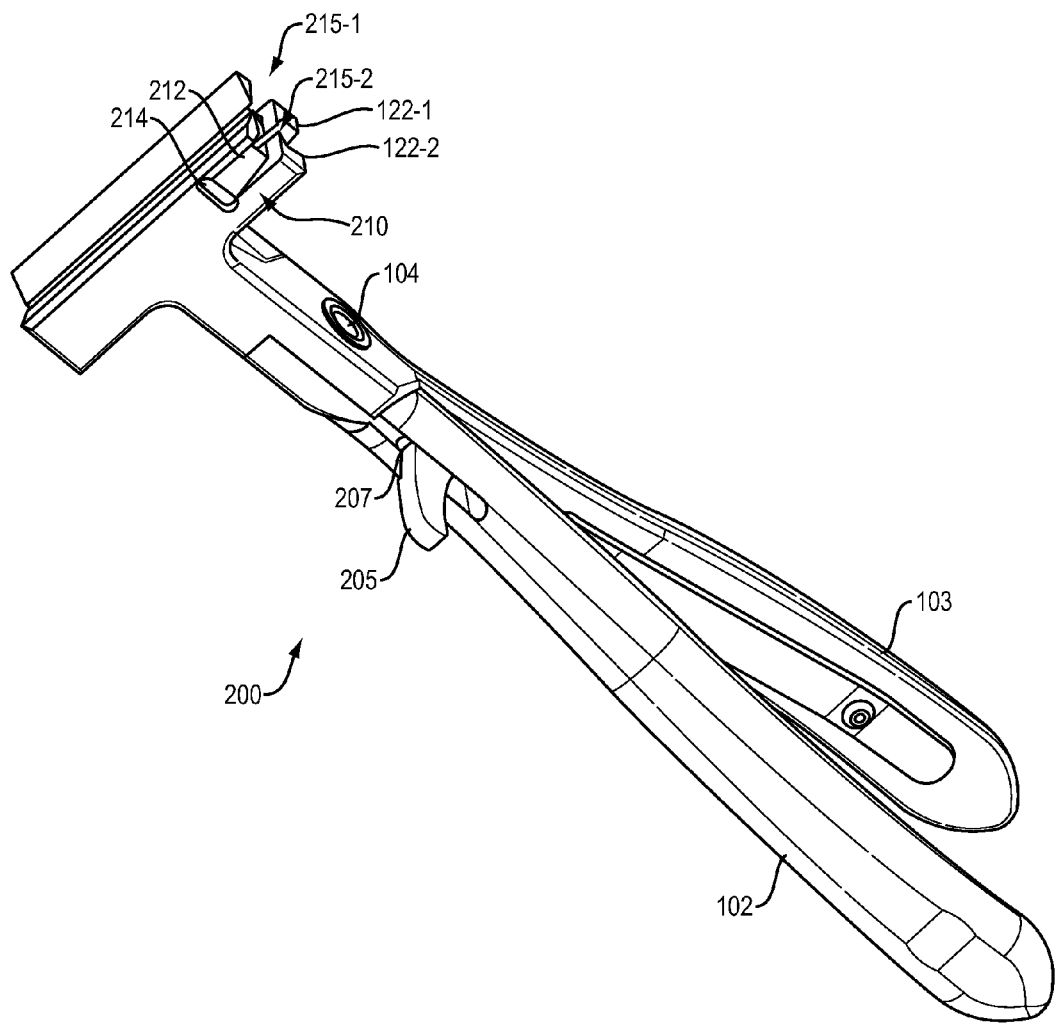
FIG. 6 is a perspective view of a compaction pliers with a latched retaining mechanism for the removable inserts.

FIG. 6 is a perspective view of a compaction pliers 200 with a latched retaining mechanism for the removable inserts. Referring to FIG. 6, the compaction pliers 200 employs a latch 210 on each compressive face 122 as a retention mechanism, rather than the threaded knobs of FIGS. 1-5. The latch 210 employs a graduated ramp surface 212 and a locking aperture 214 for engaging an insert 220, discussed further below. As in FIGS. 1-5, opposed handles 102, 103 are attached at a pivot point 104. A locking member 205 is hinged on the handle 103 for engaging a pin or slot 207 on handle 102, for fixing the handles and the articulated jaws 122 in position. Engagement slots 215-1, 215-2 (215 generally), on each respective opposed member, or jaw 122-1, 122-2 are receptive to the inserts 220.

Figure 7:
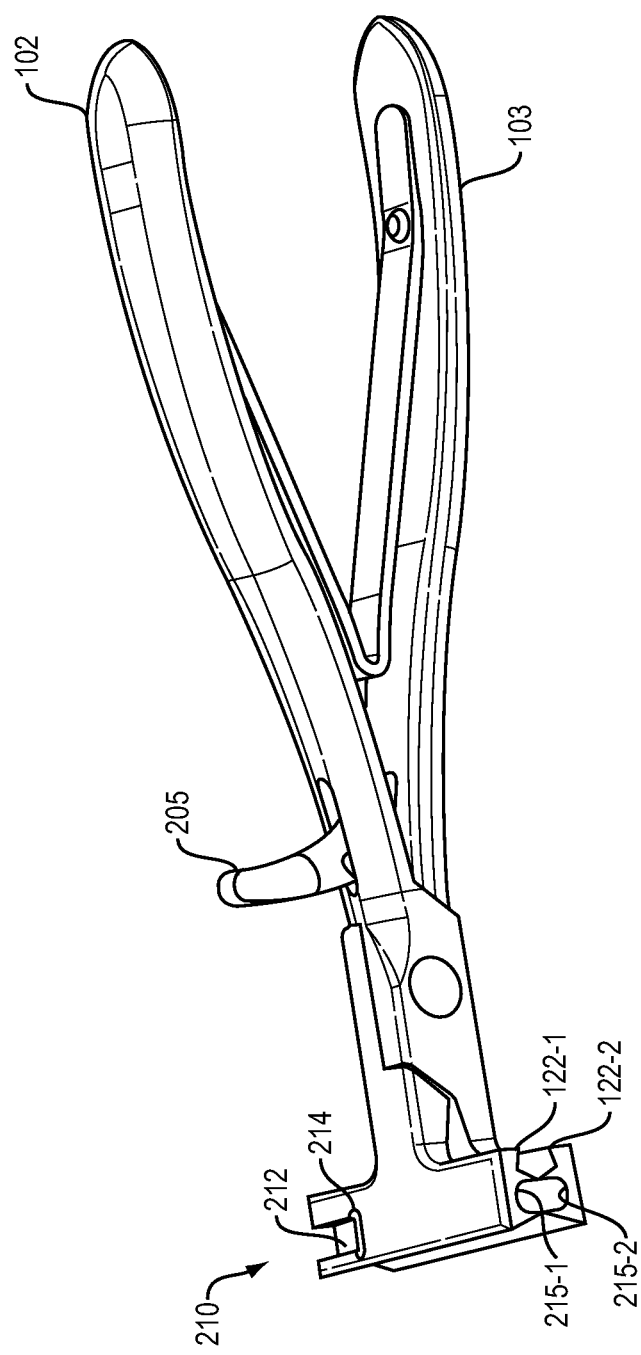
FIG. 7 is a side perspective view of the compaction pliers of FIG. 6.

FIG. 7 is a side perspective view of the compaction pliers of FIG. 6. Referring to FIGS. 6 and 7, the engagement slots 215 are shown as an annular shape receptive to a circular insert, however any suitable engagement shape could be employed.

Figure 8:
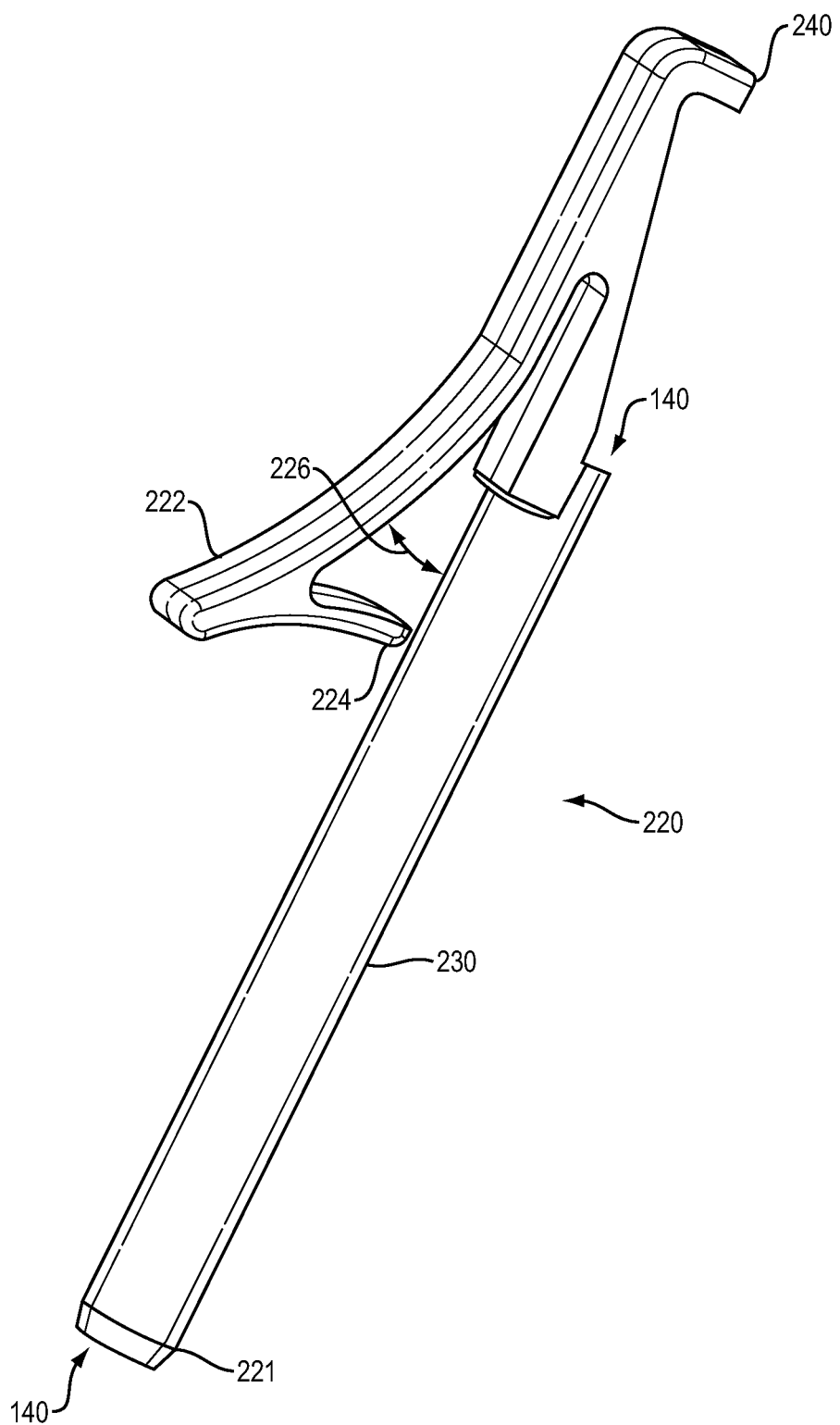
FIG. 8 is a top perspective view of a removable insert corresponding to the compaction pliers of FIGS. 6 and 7.
Figure 9:
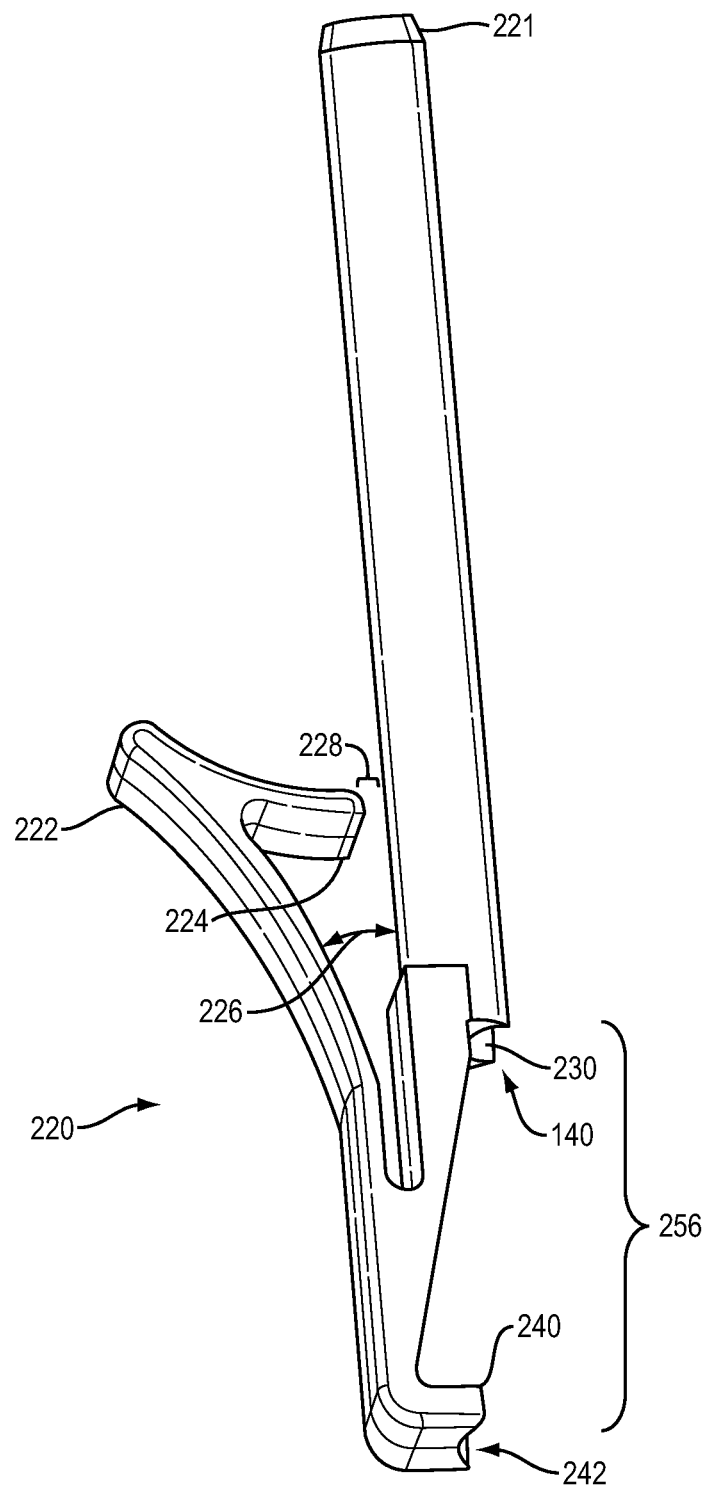
FIG. 9 is a side perspective view of the insert of FIG. 8.

FIG. 8 is a top perspective view of a removable insert corresponding to the compaction pliers of FIGS. 6 and 7, and FIG. 9 is a side perspective view of the insert of FIG. 8. Referring to FIGS. 6-9, the inserts 220 have wings 222 biased for detachable engagement with latches on the opposed compressive jaws 122. The wings 222 have tabs 224 that engage the locking aperture 214 as the insert 220 is inserted into the engagement slots 215. As the insert 220 is inserted onto the engagement slots 215 from a distal end 221 (distal end inserted first), the tabs 224 slideably contact the ramp surface 212 forcing the wing 222 away from the insert 212 as shown by arc 226. The ramp surface 212 biases the wing 222 apart a particular distance 228 to pass the edge of aperture 214, following which the biased wing 222 "snaps" the tab 224 into the aperture as the wing 222 locks the tab 224 into the aperture 214, securing the insert 220 in the engagement slot 215.

The bone graft is formed from harvested bone shaped between the inserts 220, as each of the pair of inserts 220 have complementary compressive faces 230 for enclosing the harvested bone and forming a shape engaged by the cannulated anchor, discussed further below. The inserts 220 generally define complementary pairs of faces 230 defining a circular or other shaped compression cavity 140. In the example arrangement of FIGS. 6-9, the inserts 222 define a cylindrical shape having a diameter corresponding to a diameter of a bore through the cannulated anchor that is to receive the graft. Each of the engagement slots 215 defines a receptacle that is responsive to a plurality of inserts 220, such that each of the inserts 222 corresponds to a specific bone graft size, based on the compressive faces 230 defining the compression cavity corresponding to the bone graft size. Therefore, each complementary pairs of inserts 220 defines a circular graft shape based on the bone graft size when engaged on the opposed compressive faces 230.

Each of the inserts 220 further includes a transfer tab 240 for engaging an annular groove or ridge on a transfer tube for receiving the graft, discussed further below.

Figure 10:
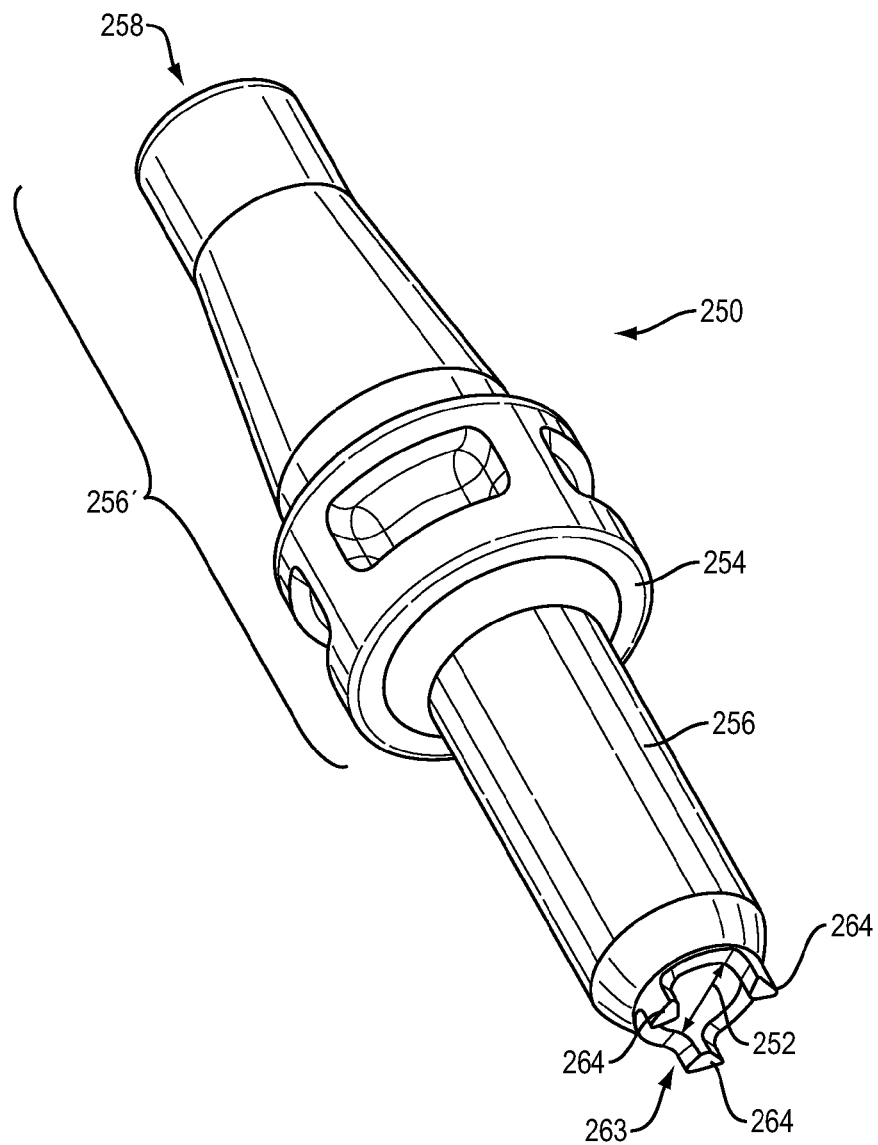
FIG. 10 is a perspective view of a transfer tube for receiving a bone graft formed by the inserts of FIGS. 8 and 9.

FIG. 10 is a perspective view of a transfer tube 250 for receiving a bone graft formed by the inserts 220 of FIGS. 8 and 9. Referring to FIGS. 8-10, the inserts 220 are adapted for engagement with a transfer tube 250 having a diameter 252 corresponding to the bore receptive to the bone graft. The transfer tube 250 also has a rotary groove or lip 254 for engagement with the inserts, such that the transfer tube 250 is adapted for receiving the cylindrical shape of the formed bone graft. The transfer tabs 240 of the respective inserts 220 draw together such that the tab 240 engages the underside of the lip 254 and an annular surface 242 of the tab 240 engages an outer surface 256 of the transfer tube 250 upon closure of the handles 102, 103, as the inserts 220 remain engaged on the slots 122. The tabs 240 define a distance 256 from the opening of the compression cavity 140 to the underside of the lip 254, matched to distance 256' such that the transfer tube is flush with the compression cavity 140 for receiving the bone graft.

Figure 11:
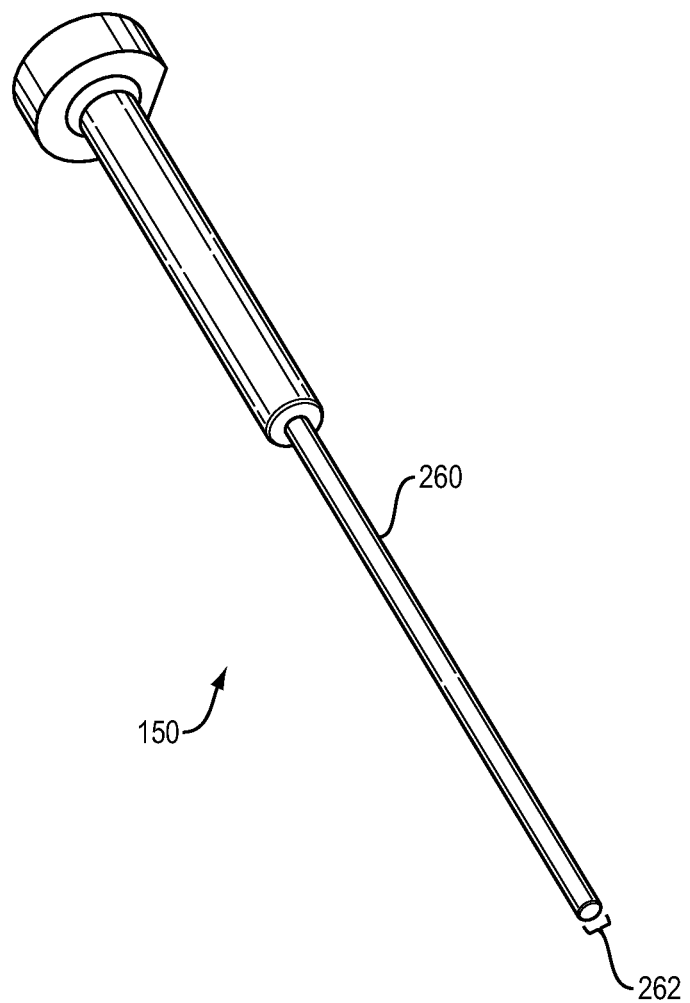
FIG. 11 is a plunger for disposing the bone graft into the transfer tube.

FIG. 11 is a plunger for disposing the bone graft into the transfer tube. Referring to FIG. 11, and continuing to refer to FIGS. 8-10, the plunger 150 has a shaft 260 with a diameter 262 corresponding to the interior of the compression cavity 140. Upon engagement of the inserts 220 with the transfer tube 250, the plunger 150 is disposed through the compression cavity 140 to transfer the formed graft into the transfer tube 250 at a proximal end 258.

Figure 12:
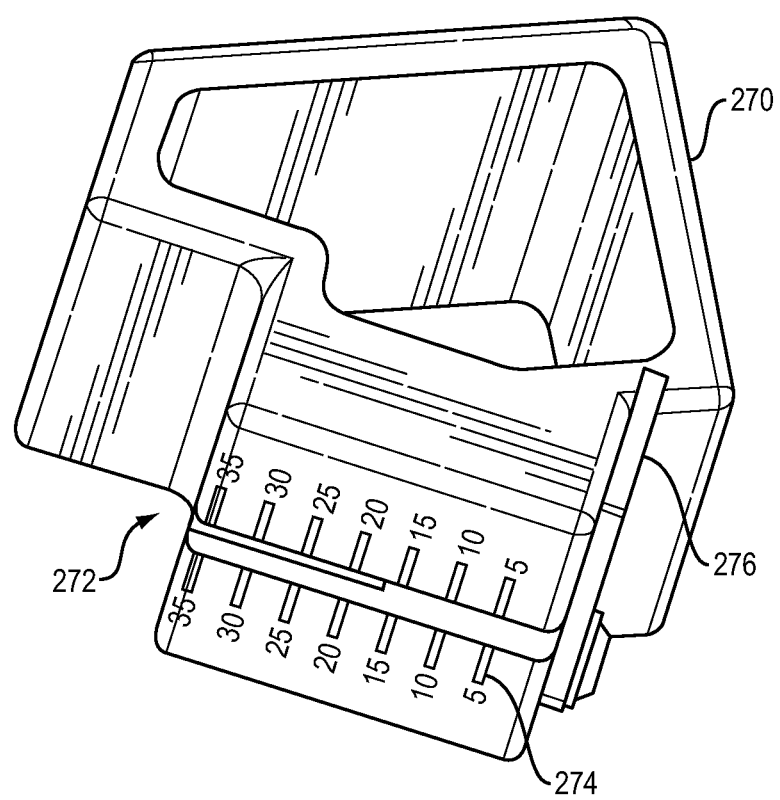
FIG. 12 is a transfer block for receiving the transfer tube of FIG. 10 and adjusting bone graft length of the graft material therein.
Figure 13:
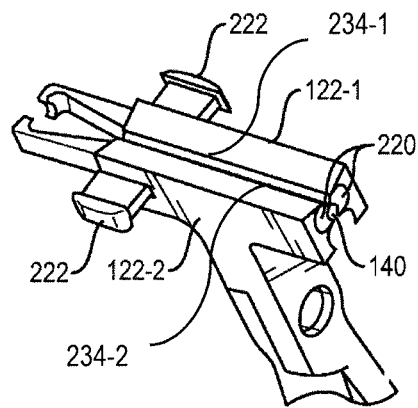
FIGS. 13-17 show usage of the disclosed device at various stages of deployment.

FIG. 12 is a transfer block 270 for receiving the transfer tube 250 of FIG. 10 and adjusting bone graft length of the graft material therein. Referring to FIGS. 8-12, once the graft is disposed in the transfer tube 250, the tube 250 is placed in a receptacle 272 in a transfer block 270. The transfer block 270 is adapted to measure the length of the bone graft, such that the block 270 acts as a base having markings 274 for ascertaining the length and the transfer tube 250 being transparent for comparing the bone graft to the markings 274. Following plunger 150 insertion of the graft into the transfer tube 250, and positioning of the transfer tube 250 in the transfer block 270, a truncation arm 276 pivots to cut any excess graft material to trim the graft to the proper length. Alternatively, the inserts 220 have cutting edges 234-1, 234-2 (FIG. 13) for severing excess shaped material.

Once graft material is fixed at the proper length in the transfer tube 250, the transfer tube 250 is disposed to the recipient anchor that was previously inserted at the surgical site. The transfer tube 250 has a mating surface 263 having protrusions 264 or other suitable alignment mechanism. The protrusions 264 correspond to a mating surface on the recipient anchor, such that the corresponding protrusions 264 maintain axial alignment along the cannulated bore for insertion of the bone graft.

Referring collectively to FIGS. 6-12, the above described apparatus provide a method for harvesting and inserting bone grafts, which may be undertaken by a surgeon or operating team for deploying the bone graft, including forming a bone graft between opposed compressive faces 230 of a compaction pliers, such that each of the opposed compressive faces 230 has a removable insert 215 corresponding to a shape of the bone graft, and transferring the bone graft to an transfer tube 250, in which the transfer tube 250 has a shape corresponding to the shape of the bone graft for receiving the bone graft into the transfer tube 250. A transfer block 270 is employed to measure, during the transfer of the bone graft, a length of the bone graft to correspond to a length of a receptive anchor for receiving the bone graft. From the proper length graft disposed in the transfer tube, the transfer tube 250 is engaged to the receptive anchor, such that the anchor has been previously inserted in a surgical site and has a cannulated bore corresponding to the shape of the bone graft. Alternatively, as indicated above, the graft may be inserted directly into a drilled bone tunnel or other surgical aperture. A plunger 150 has a shaft 260 that inserts the bone graft into the cannulated bore by disposing the shaft 260 through an opposed end of the transfer tube 250, in which the plunger corresponds to the shape of the transfer tube for driving the bone graft to a predetermined depth corresponding to the anchor.

Figure 14:
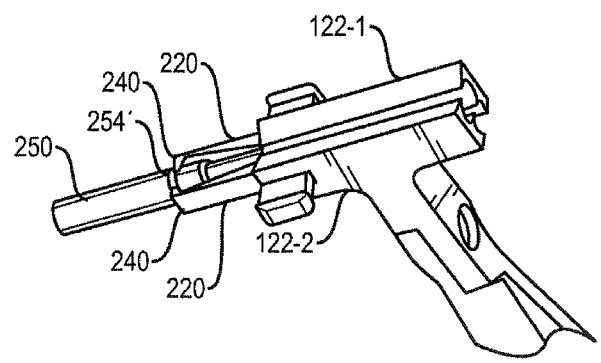
Figure 15:
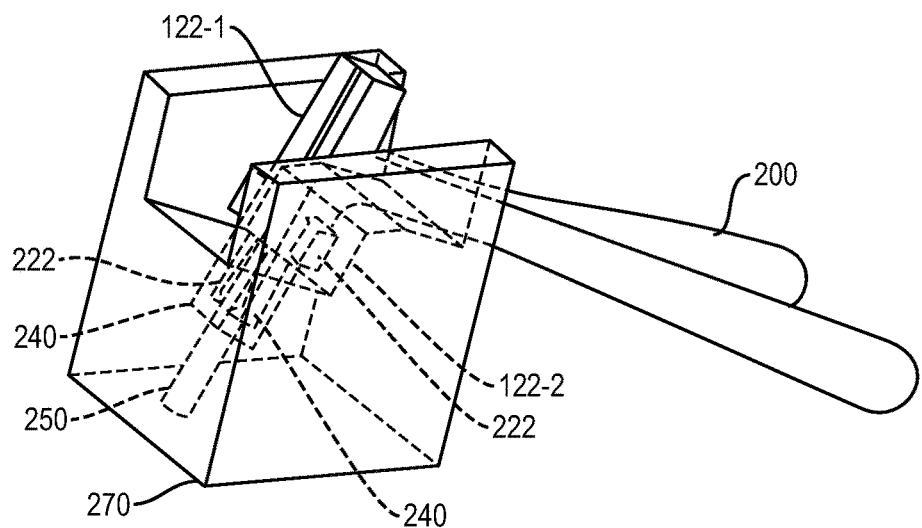
Figure 16:
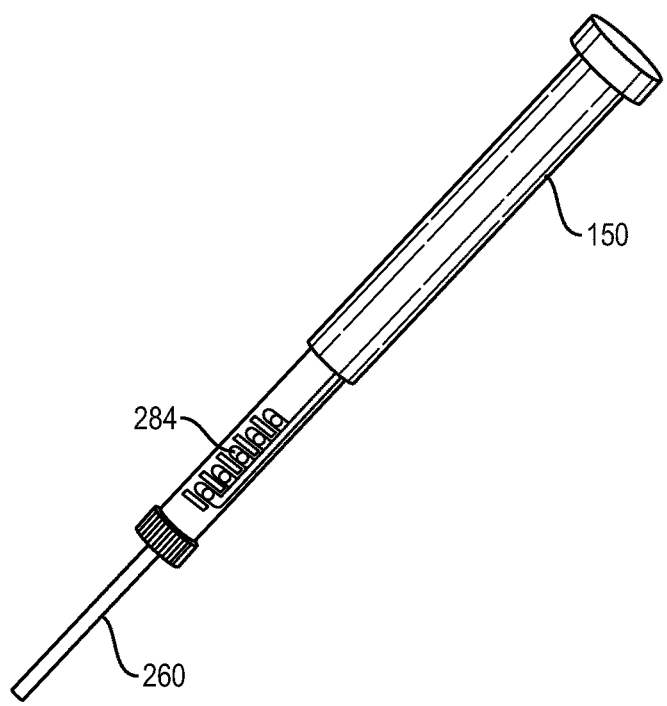

FIGS. 13-17 show usage of the disclosed device at various stages of deployment. Referring to FIGS. 6-17, FIG. 13 shows the inserts 220 engaging the jaws 122-1, 122-2 for defining the compression cavity 140. FIG. 14 shows the inserts 220 grasping the transfer tube 240 via the tabs 240 on the inserts 220. It should be noted that the transfer tube 250 employs a groove 254' as an alternative to the lip 254 of FIG. 10. FIG. 15 shows an assembly of the compaction pliers 200 engaging the transfer tube 250 (shown as a transparent/cutaway for clarity) between the inserts 222 by grasping with the tabs 240 and inserting the transfer tube 250 into the receptacle 272 in the transfer block 270. In the receptacle 272, the plunger 150 is disposed through the compression cavity 140, and has a shaft 260 which matches the diameter 252 of the inside of the transfer tube 150 for receiving the graft material. Markings 284 on the plunger, or alternatively markings 274 on the transfer block 270 are employed to ensure the proper length of the formed graft material.

Figure 17:
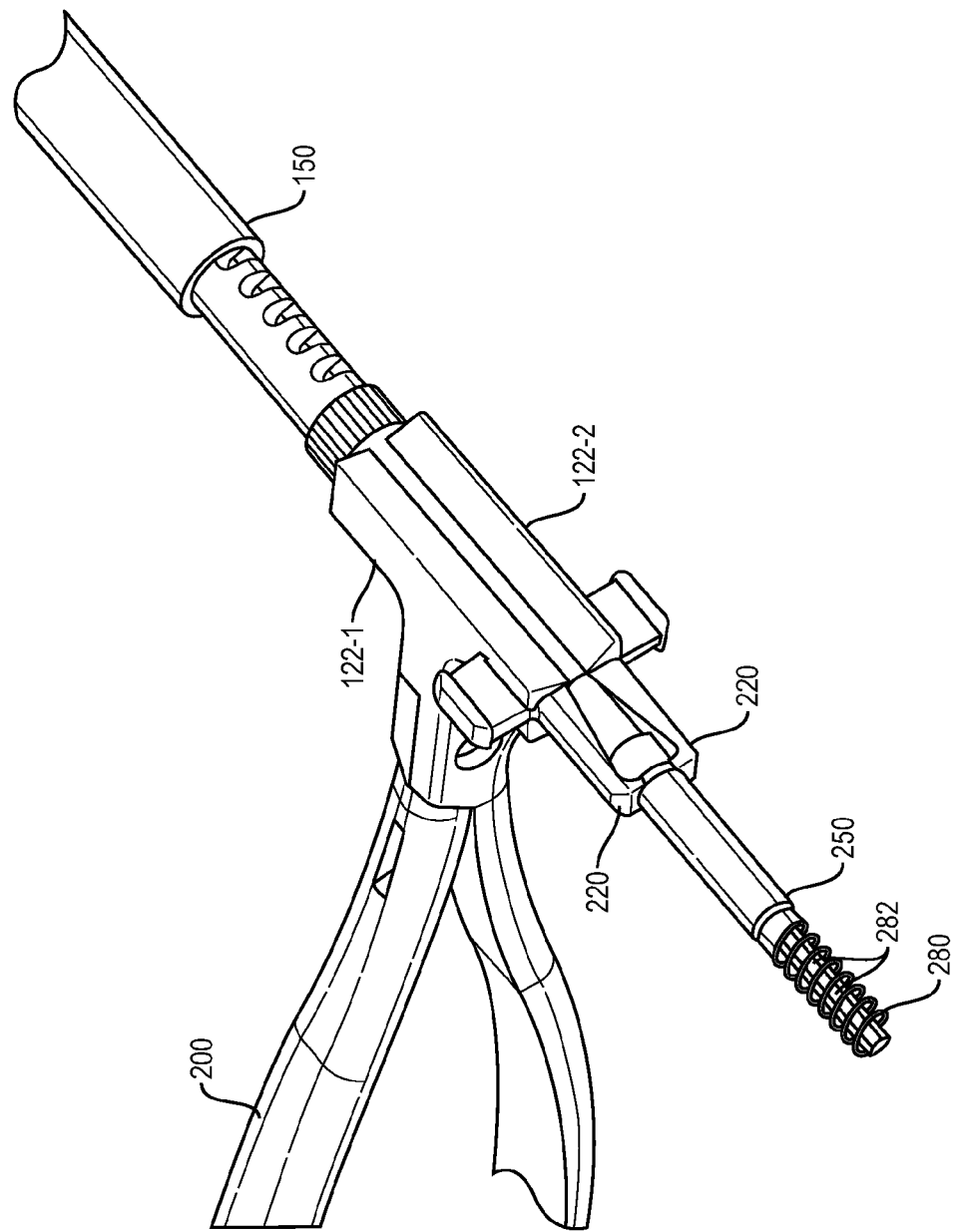

FIG. 17 shows engagement of the transfer tube 250 with the cannulated anchor 280 for insertion of the formed graft, trimmed to length. In practice, the cannulated anchor 280 would have been previously inserted in a bone tunnel. Alternatively, graft material may be deposited directly into a surgical cavity such as a bone tunnel. The plunger 150 forces the shaft 260 through the insertion tube 250, thus disposing the grant material into the cannulated anchor 280, where fenestrations 282 facilitate bone growth, facilitated by markings 284.

In the example configuration, measuring the bone graft further includes inserting the engaged compaction pliers 100 and transfer tube 250 in a transfer block 270 adapted to measure the length of the bone graft, such that the block 270 has marking for ascertaining the length and the transfer tube 250 is transparent for comparing the bone graft to the markings. The transfer tube 250 has an annular lip 254 or groove for engaging the compaction pliers 100 via the a tab 240 on the inserts 220, which provide gripping engagement for forcing the bone graft into the transfer tube by disposing the plunger 260 through a compression cavity 140 of the closed compaction pliers 100. The removable inserts 220 are adapted for latchable engagement with each of the engageable slots 214, and define a cylindrical shape adapted for insertion in a bone tunnel or cannulated bone anchor.

The transfer tube 250 has a mating surface 263 having protrusions 264, and the protrusions correspond to a mating surface on the anchor, facilitating the use of the corresponding protrusions for maintaining axial alignment along the cannulated bore for insertion of the bone graft. The anchor 280 has fenestrations 282 for facilitating bone growth with the inserted bone graft, and is inserted to a predetermined depth is such that the bone graft substantially extends through the length of the cannulated bore of the bone anchor.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A bone graft formation and insertion device comprising:
   a pair of elongated handles having proximal ends, distal ends, and a longitudinal axis extending therebetween, the handles pivotally coupled at a pivot point located between the proximal and distal ends;
   compressive jaws at distal-most ends of the handles, a length of each of the compressive jaws extending transverse to the longitudinal axis being greater than a width of each of the handles extending transverse to the longitudinal axis, the compressive jaws drawn together in a compressive engagement by closure of the handles;
   each of the compressive jaws having a receptacle;
   inserts configured for engaging the receptacles, the inserts each having a compressive face which together define a compression cavity when the respective compressive faces are brought together, the inserts further defining cutting edges extending along a length of the inserts; and
   a retention mechanism for detachable engagement with the inserts;
   wherein the device is configured to form a desired shape of a bone graft.

2. The device according to claim 1 wherein the compressive faces of the inserts comprise complementary faces for forming the shaped bone grafts.

3. The device according to claim 1, wherein the compression cavity has a cylindrical shape.

4. The device according to claim 1 wherein the retention mechanism comprises latches, and the inserts comprise wings biased for detachable engagement with the latches.

5. The device according to claim 1 wherein the inserts are adapted for engagement with a transfer tube having a rotary groove for engagement with the inserts, the transfer tube adapted for receiving the formed bone graft.

6. The device according to claim 1 further comprising a transfer block adapted to measure a length of the bone graft, the transfer block having markings for ascertaining the length.

7. The device according to claim 1 wherein the inserts have a cutting edges are configured for severing excess shaped bone graft material.

8. The device according to claim 1 wherein the inserts are slideably engageable with the jaws, and the retention mechanism comprises a locking knob for positionally fixing a respective insert to the jaws.

9. The device according to claim 8, wherein the locking knobs have a threaded engagement with the jaws.

* * * * *